United States Patent [19]

Reddy et al.

[11] Patent Number: 5,298,132

[45] Date of Patent: Mar. 29, 1994

[54] METHOD FOR MONITORING PURIFICATION TREATMENT IN PLATING BATHS

[75] Inventors: Vilambi N. R. K. Reddy, Lakewood; Bruce M. Eliash, Los Angeles; Frank A. Ludwig, Rancho Palos Verdes; Nguyet H. Phan, Los Angeles, all of Calif.

[73] Assignee: Hughes Aircraft Company, Los Angeles, Calif.

[21] Appl. No.: 37,159

[22] Filed: Mar. 25, 1993

[51] Int. Cl.$^5$ .............................................. G01N 27/26
[52] U.S. Cl. .................................. 204/153.1; 204/402; 204/412; 204/434
[58] Field of Search ............ 204/402, 412, 434, 153.1; 205/81, 101, 102, 103, 104, 105

[56] References Cited

U.S. PATENT DOCUMENTS 4,631,116 12/1986 Ludwig ............................... 204/434

Primary Examiner—John Niebling
Assistant Examiner—Bruce F. Bell
Attorney, Agent, or Firm—M. E. Lachman; M. W. Sales; W. K. Denson-Low

[57] ABSTRACT

A method for monitoring the status of a plating bath purification treatment cycle. The method involves applying a swept dc measurement signal to a pretreated electrode which is in contact with the plating solution, and monitoring the resultant response current signal. The electrode potential corresponding to the peak current density in the cathodic sweep of the response current signal provides an accurate indication of the status of the purification treatment cycle. The method tracks the progress of the purification process thereby ensuring the optimal termination points for the treatment process. The method can be used in conjunction with voltammetric plating bath analysis methods and equipment, as part of an overall plating bath monitoring and control system.

14 Claims, 2 Drawing Sheets

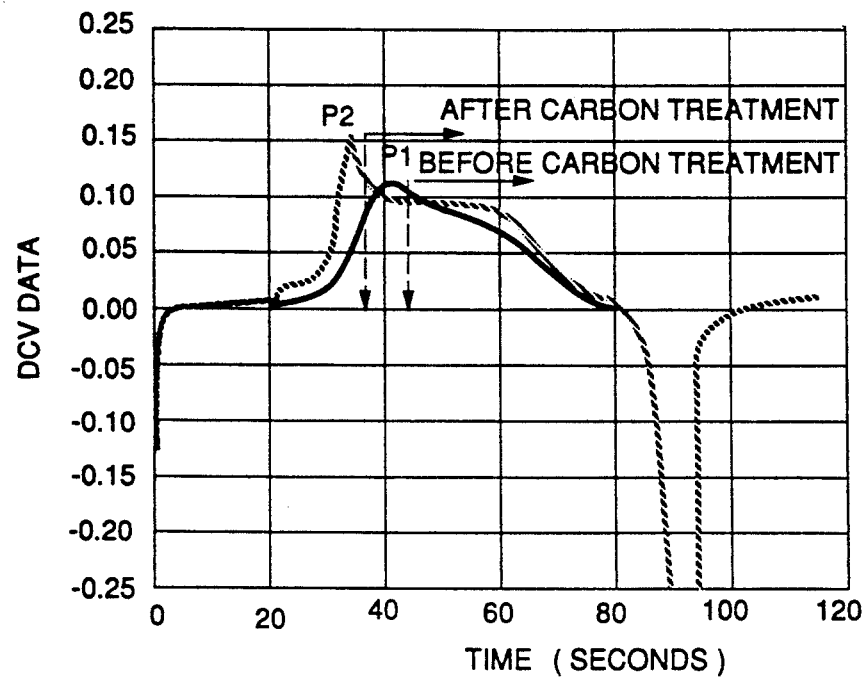
FIG. 3.
FIG. 4.
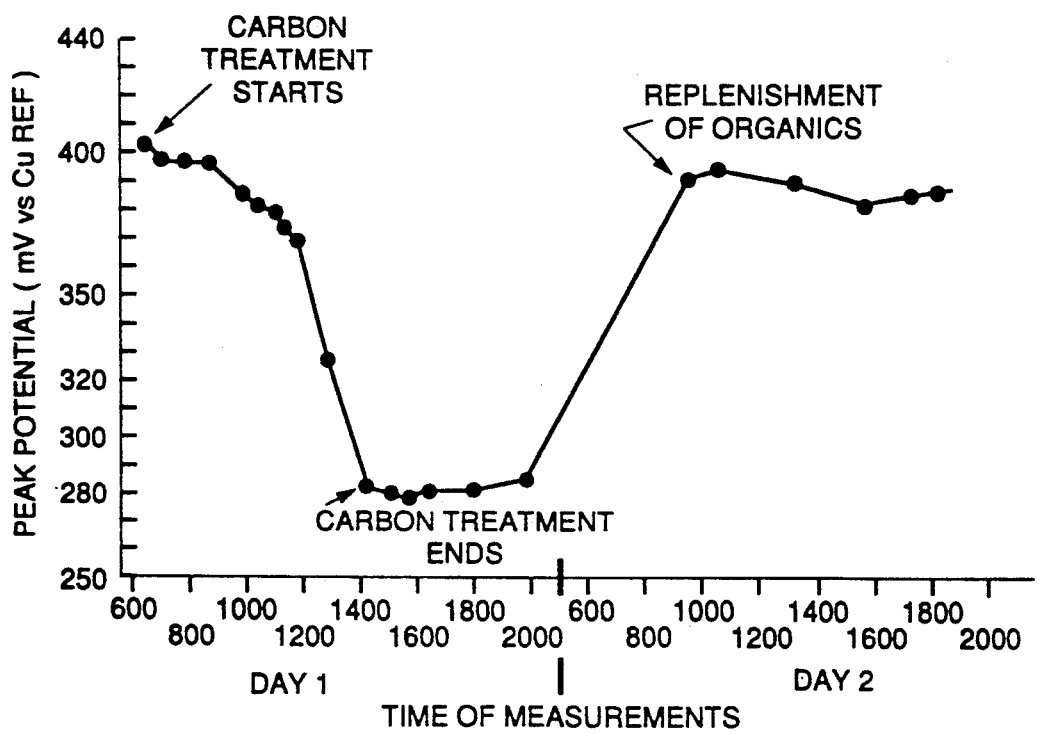

METHOD FOR MONITORING PURIFICATION TREATMENT IN PLATING BATHS

BACKGROUND OF THE INVENTION

1. Field of the Invention

The present invention relates to plating bath analysis methods. More particularly, the present invention relates to a method for monitoring the status of a plating bath purification treatment cycle.

2. Description of Related Art

To ensure optimal performance of a plating bath, the bath must be purified at regular intervals. The purification serves to remove organic contaminants and other impurities which can build up in the bath over time and lead to undesirable plating characteristics. In many cases, the contaminants are breakdown products resulting from the electrochemical processes within the bath. The time between purification treatments varies depending upon the contaminant buildup rate, which is a function of the nature and frequency of the plating bath processes. For example, plating baths using organic addition agents such as the acid copper plating bath generate significant levels of contaminants and require frequent purification.

Carbon treatment is one widely used plating bath purification technique. The carbon treatment process involves contacting activated carbon with the plating bath. The contaminants are adsorbed on the activated carbon and thereby effectively removed from the plating bath solution. The level of contaminants within the bath is continually reduced during the purification treatment, and when an acceptably low contaminant level is attained, the treatment can be terminated. Fresh addition agents are added to the treated bath and the plating bath is ready for use again. On continued usage organics and other contaminants will again begin to accumulate within the bath, and the purification treatment will eventually have to be repeated. Since the quality of the plating bath depends upon maintaining a low level of contaminants, it is essential that the carbon treatment cycles be initiated and terminated at the appropriate times. The same concerns apply to other plating bath purification techniques.

Under current practice, the progress of the purification treatment is typically monitored by repeated manual tests on the plating bath solution. One such manual test, disclosed in LeaRonal Application Note No. AN30009CT, uses a Hull cell plating technique to monitor carbon treatment. During the carbon treatment process, an operator will run a Hull cell plating test approximately once every three hours to determine when the process is complete. Each Hull cell test is performed at 2 amperes for 15 minutes with air agitation. When the plated Hull cell panels appear flat-matte across the entire current density range, the carbon treatment process is considered sufficiently complete. Other methods currently used involve similar repeated manual testing procedures.

The current purification treatment monitoring methods suffer from a number of problems. Repeated performance of manual tests is time-consuming and requires skilled personnel and specialized equipment. The time required to perform the tests translates into production downtime, thereby limiting plating process productivity.

In addition, presently used techniques do not usually lead to accurate and repeatable results. The manual tests often involve guess work and arbitrary interpretation, as in the case of the plated Hull cell panels. This can lead to incomplete purification treatments and resultant plating bath quality problems.

Furthermore, present techniques are not easily integrated with known voltammetric plating bath analysis methods, such as those disclosed in U.S. Pat. No. 4,631,116, and assigned to the present common assignee. Plating bath users must therefore maintain one system and set of equipment for measuring plating bath constituent concentration, and another for tracking the progress of purification treatments.

As is apparent from the above, there presently is a need for a simple and efficient method of continuously monitoring the status of a purification treatment cycle within a plating bath. The method should provide a highly accurate indication of the optimal treatment initiation and termination points. The method should provide these features and also be compatible with most on-line plating bath analysis methods and the equipment associated therewith.

SUMMARY OF THE INVENTION

The present invention is based upon the discovery that voltammetric techniques can provide an accurate indication of the progress of plating bath purification treatments. Voltammetric techniques have been used to monitor plating bath trace constituent concentrations, such as those disclosed in U.S. Pat. No. 4,631,116, but have not heretofore been considered for monitoring purification treatment status.

The present invention provides a method for monitoring plating bath purification treatment cycles. The method includes the steps of providing an electrode in contact with the plating bath solution, applying a dc pretreatment signal to the electrode in order to remove organics and other contaminants from its surface, and applying a swept dc measurement signal to the pretreated electrode such that a response current signal is produced. Response current signal characteristics are then monitored to determine plating bath contaminant level and thereby the status of the purification treatment cycle.

As a feature of the present invention, the steps of applying the pretreatment and measurement signals, and monitoring the response current, are repeated often enough during the purification treatment to accurately determine the optimal treatment termination point. These same steps can also be repeated during normal plating operation before or after the purification treatment to determine the optimal treatment initiation point. The decision as to whether or not to initiate or terminate a purification treatment process is based upon the plating bath contaminant concentration level as indicated by the response current.

As an additional feature of the present invention, the method provides highly accurate and repeatable measurement results. The purification treatment process is initiated and terminated at a predetermined contaminant level. Plating bath contaminant levels are thereby continuously maintained at desired low levels, ensuring optimal plating process throughput and quality.

As a further feature of the present invention, the method can be used with an in-tank electrochemical sensor to provide results in real time without interfering with the normal operation of the plating bath. Production downtime for time-consuming manual testing is thereby eliminated.

The monitoring method of the present invention may be performed using the same equipment and instrumentation typically used with voltammetric plating bath analysis methods. Special test equipment used solely for monitoring purification treatment is no longer required. The method of the present invention can thus be easily integrated with known plating bath analysis techniques to provide an efficient overall electrochemical monitoring and control system.

The above-discussed features and attendant advantages of the present invention will become better understood by reference to the following detailed description of the preferred embodiment and the accompanying drawings.

BRIEF DESCRIPTION OF THE DRAWINGS

FIG. 3 shows exemplary response current signals generated in accordance with the preferred embodiment of FIG. 1 for a carbon treatment purification cycle.

FIG. 4 shows an exemplary compilation of response signals taken over an entire carbon treatment purification cycle.

DETAILED DESCRIPTION OF THE PREFERRED EMBODIMENT

Voltammetric techniques have been used to detect the concentration levels of various plating bath electrochemical constituents. One exemplary voltammetric technique, disclosed in Delahay, "New Instrumental Methods in Electrochemistry", Chap. 6, Interscience Publisher Inc., 1966, uses a linearly swept dc voltammetry signal. Other methods, such as those disclosed in U.S. Pat. No. 4,631,116, use both ac and dc voltammetric signals. However, none of these ac or dc voltammetry techniques have heretofore been considered for monitoring the status of plating bath purification treatments.

In accordance with the present invention, voltammetric techniques are applied to monitoring the purification of plating baths. An exemplary purification cycle is shown in FIG. 4. The following detailed description is directed to an exemplary carbon treatment purification cycle monitored using a preferred linear dc sweep voltammetry technique. However, it should be noted that the present invention is not limited to this exemplary treatment or technique. The method can also be used to monitor a variety of different purification treatments using other ac and dc voltammetric techniques.

Figure 1:
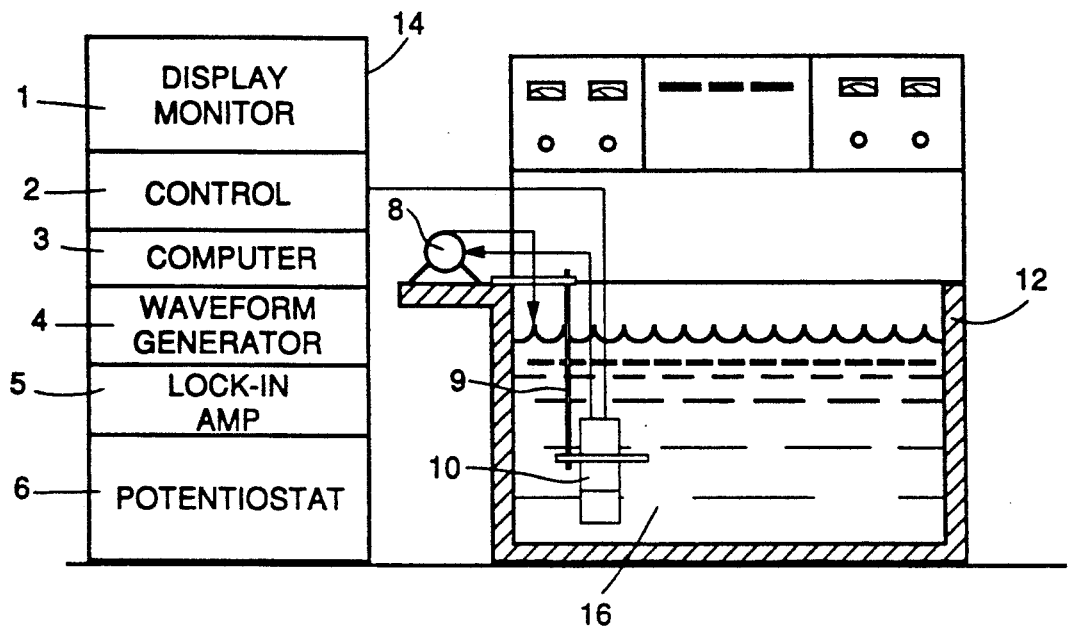
FIG. 1 shows a preferred embodiment of exemplary equipment for conducting the method of the present invention.

A preferred embodiment of equipment for conducting the method of the present invention is shown in FIG. 1. The preferred embodiment includes an in-tank electrochemical sensor 10 immersed in a plating tank 12 filled with electrochemical liquid 16. The in-tank sensor 10 is held within the tank 12 by support 9. External pump 8 moves electrochemical liquid 16 through the sensor 10 for measurement. An external test equipment rack 14 includes a display monitor 1, a control unit 2, a computer 3, a waveform generator 4, a lock-in amplifier 5, and a potentiostat 6. The waveform generator 4 and potentiostat 6 generate the voltammetric signals which are applied to electrodes within the sensor 10. The computer 3 and control unit 2 can serve to automate the generation and display of the measurement and response signals.

Figure 2:
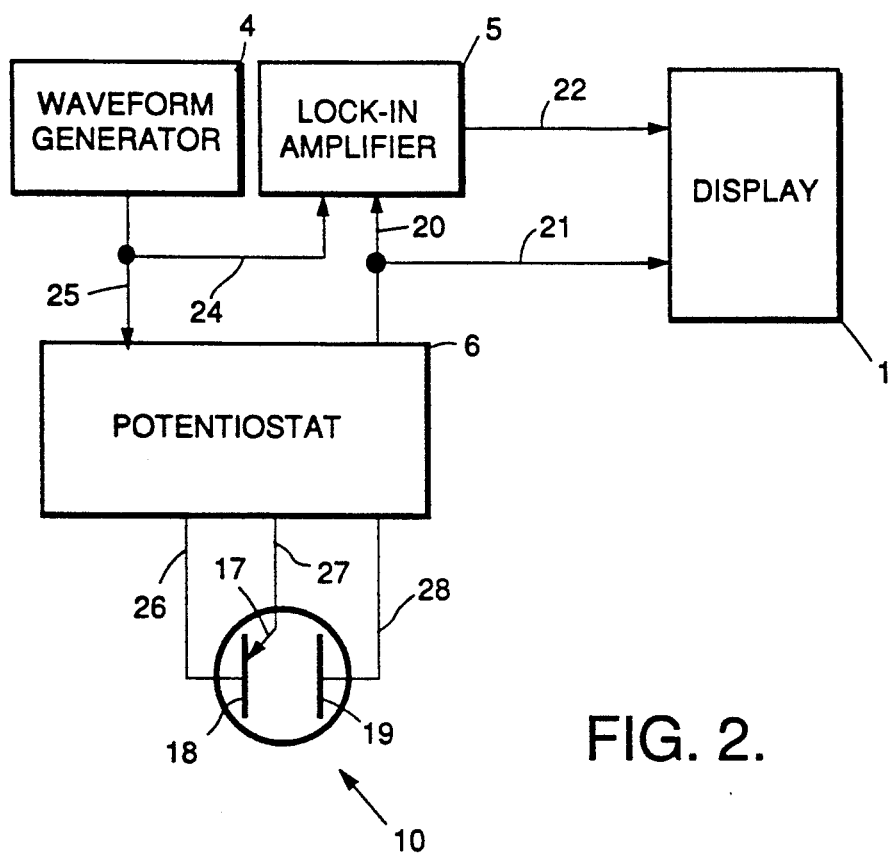
FIG. 2 is a schematic diagram of the preferred embodiment of FIG. 1.

The operation of the equipment shown in FIG. 1 can be better understood by reference to the schematic diagram of FIG. 2. The exemplary in-tank electrochemical sensor 10 contains a working electrode 18, counter electrode 19, and reference electrode 17, all of which are in contact With the electrochemical liquid 16. Prior to measurement, a pretreatment signal is applied to the working electrode in order to remove any adsorbed organic materials or other contaminants on its surface. Voltammetric measurement signals are then applied to the pretreated working electrode 18. The response current signal generated is then measured as a function of the working electrode potential. The working and counter electrodes 18, 19 may be constructed of platinum, copper, gold, silver or other suitable conductive material. The reference electrode 17 is typically a copper electrode or a saturated calomel electrode (SCE). The in-tank electrochemical sensor 10 with electrodes 17, 18 and 19 is a sensor design typically used in conjunction with voltammetric techniques. Other sensor designs could also be used.

Waveform generator 4 provides appropriate pretreatment and measurement signals. The pretreatment signal is typically a constant dc signal applied for a predetermined period of time. Alternatively, the pretreatment signal may be supplied directly from potentiostat 6. The measurement signal can be a dc sweep signal, a suitable ac signal or a combination of ac and dc signals, depending upon the type of voltammetric technique being used. For example, if the voltammetric techniques disclosed in U.S. Pat. No. 4,631,116 are used, the output signal from waveform generator 4 would preferably be a sinusoidal ac signal which is then superimposed on a dc sweep signal generated in the potentiostat 6. In the present preferred embodiment, which uses linear dc sweep voltammetry, the waveform generator 4 supplies a dc sweep signal to potentiostat 6 as represented by line 25. Alternatively, a dc sweep signal can be generated within the potentiostat 6.

The dc sweep signal output from potentiostat 6 is applied to the working electrode 18 in the electrochemical sensor 10 via line 26. The counter electrode 19 and reference electrode 17 are connected to potentiostat 6 via lines 28, 27, respectively. When the dc sweep signal is applied to the working electrode 18, a response current is generated between the working electrode 18 and the counter electrode 19. The potentiostat 6 serves to ensure that the characteristics of the applied dc sweep signal do not vary as a result of variations in current flow between the working electrode 18 and counter electrode 19.

The response signal is the dc current measured as a function of the applied potential. All potentials measured are with reference to the reference electrode. The diagnostic signal which tracks the purification of the plating bath is the electrode potential corresponding to the dc peak current density in the cathodic sweep. Two exemplary response current signals generated using the preferred embodiment of the present invention are shown in FIG. 3. These current response signals are displayed as a function of time, but could also be displayed as a function of another signal characteristic, such as sweep potential.

The specific equipment used in the exemplary system of FIGS. 1 and 2 includes an Hp Model 3314A waveform generator, a PAR 273 potentiostat, and a PAR 5208 lock-in amplifier. The HP waveform generator is available from Hewlett-Packard Co., of Fullerton, Calif. and the PAR equipment is available from Princeton Applied Research, of Princeton, N.J.

In order to ensure the accuracy of the response current spectra produced in accordance with the exemplary voltammetric technique and equipment described above, optimal pretreatment and measurement signal parameters should be used. For the linear dc voltammetric technique of the present preferred embodiment, the dc pretreatment voltage and time as well as dc sweep signal voltage range and sweep rate have been independently varied to determine optimal settings. A dc pretreatment signal with a voltage potential of about +2.0 to +3.0 volts is preferably applied to the working electrode for a period of about 5 to 20 seconds. A dc sweep measurement signal with a sweep potential ranging from about +3 V to −3 V, a sweep rate of about 10 to 100 mv/sec, and reversed at a potential of about −0.2 to −0.6 volts is then applied to the working electrode.

It should be emphasized that while the parameter settings described above are optimal, the method may produce useful results using parameters outside these specified optimal ranges. In applying other voltammetric techniques in accordance with the method of the present invention, a set of optimal parameters applicable to the particular technique would be used.

The above pretreatment and measurement signals are applied to the working electrode 18 at regular intervals throughout the purification treatment process. During the treatment process, more frequent measurement is appropriate in order to minimize the treatment time. Preferably, the measurements are repeated about every 0.1 to 0.5 hours during the treatment until acceptably low levels of contaminants are achieved. Once the treatment process is complete, the plating bath will exhibit acceptably low levels of contaminants.

The above described determination of measurement signal intervals is well suited to computer control. The computer 3 and control unit 2 may be used to provide automatic control of the purification monitoring process. The computer can store time periods and measurement results from prior cycles to determine optimal measurement intervals for subsequent cycles. Furthermore, optimal measurement intervals for particular types of plating baths or purification processes may be stored within the computer and used as needed, resulting in a highly efficient and flexible purification monitoring process.

The preferred embodiment described above is applied to carbon treatment purification of an acid copper plating bath in the following example. All voltages discussed in conjunction with this example are relative to a copper reference electrode. A platinum working electrode was pretreated using a constant dc signal with a voltage potential of about +3 V for a period of about 10 seconds. The measurement signal was a dc sweep signal with a sweep potential ranging from about +0.5 volts to about +0.6 volts, a sweep rate of about 20 mv/sec, and reversed at a potential of about −0.4 to −0.6 volts. These signals were generated and applied to the acid copper plating bath in accordance with the preferred embodiment described above.

The steps of applying pretreatment and measurement signals and monitoring response signals were repeated before, during and after an exemplary carbon treatment. The two resultant response current signals corresponding to the beginning and end of the carbon treatment are displayed as a function of time in FIG. 3. In FIG. 3, the term "DCV data" indicates the signal output in volts from the potentiostat, which is a measure of the dc current. The response current signal taken immediately before the start of the carbon treatment has a peak P1 at about 41 seconds. The voltage potential corresponding to this peak is about 400 mv. This measurement corresponded to the condition of the plating bath prior to carbon treatment. Subsequent measurements, as shown in FIG. 4, exhibit a decreasing peak potential as the carbon treatment progresses. Eventually, a point is reached at which the carbon treatment can be terminated. The response current corresponding to this point is shown in FIG. 3 and has a potential peak of about 280 mv at about 35 seconds. This measurement corresponded to the condition of the plating bath at the end of carbon treatment.

The variation in potential corresponding to the diagnostic peak current density across all of the response current measurements taken on this exemplary cycle is shown in FIG. 4. In FIG. 4, the "Time of Measurement" indicates the time during the process of carbon treatment and replenishment of organics at which the measurement was made. The time is indicated in clock time over a two-day period. The response current potential peaks P1 and P2 in FIG. 3 correspond to measurement points P1 and P2 in FIG. 4, respectively.

As shown in FIG. 4, the carbon treatment lasted about 8 hours, indicated by the time difference between points P1 and P2. Measurements during the treatment are repeated at relatively frequent intervals of about 0.1 to 0.5 hours. The measurements can thus provide an accurate and easy means of monitoring the plating bath purification process quantifying the organic content of the plating bath. The method of the present invention can be similarly applied to a variety of different plating baths and purification treatments using other voltammetric techniques.

It will be understood by those skilled in the art that the foregoing description is by way of example only, and that many variations are possible without deviating from the scope of the present invention, which is limited only by the following claims.

What is claimed is:

1. A method for monitoring a purification treatment cycle within a plating bath solution, said method comprising the steps of:

providing at least one electrode in contact with said plating bath solution;

applying a dc pretreatment signal to said electrode, said dc pretreatment signal having a selected potential and selected duration to pretreat said electrode by removing any adsorbed organic materials or other contaminants from said electrode;

applying a swept dc measurement signal to said pretreated electrode, said dc measurement signal having a sweep potential, a sweep rate and a reversal potential, and producing a response current signal; and monitoring the characteristics of said response current signal;

wherein said response current signal characteristics provide an accurate indication of the status of said plating bath purification treatment cycle.

2. The method of claim 1 wherein said steps of applying said pretreatment and said measurement signals to said electrode and said step of monitoring said response signal characteristics are repeated about every 0.1 to 0.5 hours during the purification treatment.

3. The method of claim 1 wherein said purification treatment cycle is a carbon treatment cycle.

4. The method of claim 1 wherein said electrode is formed from a metal selected from the group consisting of platinum, gold and silver.

5. The method of claim 1 wherein said pretreatment signal potential is about +2.0 to +3.0 volts and said pretreatment signal duration is about 5 to 20 seconds.

6. The method of claim 1 wherein said measurement signal sweep potential ranges from about +3.0 to −3.0 volts.

7. The method of claim 1 wherein said measurement signal sweep rate is about 10 to 100 mv/sec and further wherein said measurement signal reversal potential is about −0.2 to −0.6 volts.

8. The method of claim 1 wherein one of said response signal characteristics is the electrode potential corresponding to the peak current density of said response current signal in the cathodic sweep.

9. The method of claim 1 further providing automatic control circuitry to determine when said purification treatment should be terminated based upon said characteristics of said response current signal, and to then terminate said treatment.

10. The method of claim 1 wherein said electrode is contained within an in-tank electrochemical sensor used in conjunction with a plating bath analysis method, and further wherein said pretreatment, measurement and response signals are provided and monitored by the same external equipment used in said plating bath analysis method.

11. A method for monitoring a purification treatment cycle within a plating bath solution, said method comprising the steps of:
providing at least one electrode in contact with said plating bath solution;
applying a pretreatment signal to said electrode, said pretreatment signal having a selected potential and a selected duration to pretreat said electrode by removing any adsorbed organic materials or other contaminants from said electrode;
applying a voltammetric signal to said electrode after said pretreatment signal, said voltammetric signal producing a response current signal, said response current signal having characteristics indicative of levels of organic constituents within said plating bath;
monitoring said characteristics of said response signal; and
repeating said steps of applying said pretreatment and voltammetric signals to said electrode and said step of monitoring said response current characteristics, at selected intervals so as to determine the optimal termination points of said purification treatment cycle.

12. The method of claim 11 wherein said purification treatment cycle is a carbon treatment cycle.

13. The method of claim 11 further providing automatic control circuitry to determine when said purification treatment should be terminated based upon said characteristics of said response current signal, and to then terminate said treatment.

14. The method of claim 11 wherein said electrode is contained within an in-tank electrochemical sensor used in conjunction with a plating bath analysis method, and further wherein said pretreatment, measurement and response signals are provided and monitored by the same external equipment used in said plating bath analysis method.

* * * * *